(12) United States Patent
Kane et al.

(10) Patent No.: US 7,003,436 B1
(45) Date of Patent: Feb. 21, 2006

(54) DETERMINATION OF FIT BASIS FUNCTIONS

(75) Inventors: Daniel J. Kane, Santa Fe, NM (US); David Christian Hovde, Cincinnati, OH (US)

(73) Assignee: Southwest Sciences Incorporated, Santa Fe, NM (US)

( * ) Notice: Subject to any disclaimer, the term of this patent is extended or adjusted under 35 U.S.C. 154(b) by 411 days.

(21) Appl. No.: 10/310,259

(22) Filed: Dec. 4, 2002

(51) Int. Cl.
*G06F 11/00* (2006.01)
(52) U.S. Cl. ...................................... 702/189; 356/300
(58) Field of Classification Search ................ 702/189, 702/188; 356/301, 246, 300; 438/9
See application file for complete search history.

(56) References Cited

U.S. PATENT DOCUMENTS 5,450,193 A * 9/1995 Carlsen et al. .............. 356/301

OTHER PUBLICATIONS

D. Broomhead, et al. "Extracting qualitative dynamics from experimental data," *Physica* 20D, pp. 217-236 (1986).

A. Jain, *Fundamentals of Digital Image Processing*, Prentice Hall Information and Systems Sciences Series, Prentice Hall, Englewood Cliffs (1989).
W. Press, et al., *Numerical Recipes in C: The Art of Scientific Computing*, 2d ed., Cambridge University Press, Cambridge; pp 51-63 (1995).
M. Richman, "Rotation of Principal Components", *Journal of Climatology* 6:393-335 (1986).
G. Stewart, "Perturbation Theory for the Singular Value Decomposition", University of Maryland Computer Science Technical Report CS-TR-2539 (1990).

* cited by examiner

*Primary Examiner*—Edward Raymond
(74) *Attorney, Agent, or Firm*—Jeffrey D. Myers; Peacock Myers P.C.

(57) ABSTRACT

An apparatus, software, and method for segregating out background signals from a signal of interest comprising sampling a signal that includes the background signals over one or more periods of time, forming a matrix from results of the sampling, calculating a matrix of basis functions via a singular value decomposition of the matrix from the forming operation, and determining a set of basis functions to employ to segregate out background signals. Also a corresponding wavelength modulation spectroscopy apparatus, software, and method.

25 Claims, 6 Drawing Sheets

Comparison of parts-per-billion water measurement with and without using SVD basis determination.

Fig. 1. Diode laser absorption apparatus

Fig. 2. Sample 2f Spectra

Fig. 3. First Basis Function

Fig. 4. Basis Function Weights

Fig. 5. Second Basis Function

Fig. 6. Third Basis Function

Fig. 7. Fourth Basis Function

Fig. 8. Fifth Basis Function

Fig. 9. Sixth Basis Function

Fig. 10. The 2f spectrum of the absorber is the seventh basis function. The coefficient determined from the least squares fit for this basis function is directly related to the amount of absorption due to water vapor, and hence the water vapor concentration.

Fig. 11. Comparison of parts-per-billion water measurement with and without using SVD basis determination.

DETERMINATION OF FIT BASIS FUNCTIONS

BACKGROUND OF THE INVENTION

Field of the Invention (Technical Field)

The present invention relates to determination of basis functions for fitting procedures used to measure quantities related to a fit, such as for removing interference from trace gas detection using wavelength modulation spectroscopy.

SUMMARY OF THE INVENTION (DISCLOSURE OF THE INVENTION)

The present invention is of an apparatus, software, and method for segregating out background signals from a signal of interest, comprising: sampling a signal that includes the background signals over one or more periods of time; forming a matrix from results of the sampling; calculating a matrix of basis functions via a singular value decomposition of the matrix from the forming operation; and determining a set of basis functions to employ to segregate out background signals. In the preferred embodiment, the invention additionally comprises including the signal of interest in the set. The resulting set of basis functions may be used to remove background signals from a subsequent measurement of a signal combining the background signals and the signal of interest. The sampling, forming, calculating, and determining steps may periodically be reexecuted as the background signals become altered. The set of basis functions may also be employed to analyze one or more likely sources of one or more background signals. An input may be altered over the one or more periods of time, thereby affecting the combined signal, such as by changing current supplied to a laser of a wavelength modulation spectroscopy device and sampling by measuring light intensity at a harmonic frequency of frequency generated by the laser, preferably the second harmonic frequency. Forming preferably occurs by dividing a matrix from the results of the sampling step by a matrix of current supplied to the laser.

The invention is also of an apparatus, software, and method for segregating out background signals from a signal of interest generated from a wavelength modulation spectroscopy device, comprising: sampling a signal that includes the background signals over one or more periods of time while changing current supplied to a laser of the wavelength modulation spectroscopy device; forming a matrix from results of the sampling; calculating a matrix of basis functions via a singular value decomposition of the matrix from the forming operation; and determining a set of basis functions to employ to segregate out background signals. The preferred embodiment is as described in the preceding paragraph.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 1 is a schematic of a wavelength modulation spectroscopy apparatus 10 using a diode laser 12 as the spectroscopic source. The laser is driven by a bias current 24. Imposed on the bias current is a sine wave modulation current 20 and a ramp current 22. The sine wave and the ramp tune the diode laser in wavelength to generate an absorption spectrum. The output from the diode laser is passed through a sample 14 to measure. The output of a detector 16 is demodulated 26 with the second harmonic 18 of the sine wave modulation imposed on the laser. The filtered signal 28 is similar to the second derivative of the line shape of the measured absorption. An ideal signal has no background artifacts. A typical signal spectrum, especially when measuring small absorbances, has many artifacts that can interfere with the measurement of the absorber species.

FIG. 6 is a plot of the third basis function. This basis function has a strong etalon component. By determining the frequency of the etalon, the spacing of the optical components involved can be determined. If these etalons are determined to cause problems with the measurement, the cause of these etalons can be found and corrected.

FIG. 7 is a plot of the fourth basis function. The sine wave in this plot is roughly 90 degrees out of phase from the etalon shown in FIG. 6. This is to be expected from an etalon that has a phase that drifts as a function of time. From the relative magnitudes of these two etalons, the drift rate can be determined.

DESCRIPTION OF THE PREFERRED EMBODIMENTS (BEST MODES FOR CARRYING OUT THE INVENTION)

The present invention is of a method to determine basis functions for fitting procedures used to measure quantities related to a fit. A model of the data to be fit is supplied and a singular value decomposition is used to determine the basis functions to describe the background. The preferred embodiment of this method is for determination of the basis functions of a background that interferes with the measurement of a desired quantity. An example, discussed in depth herein, is to employ the invention to remove interferences from trace gas detection using wavelength modulation spectroscopy.

One way to measure trace absorptions is to wavelength modulate an optical source across a spectral feature. Because the wavelength of the optical radiation crosses the spectral absorption twice during each modulation cycle, a second harmonic signal proportional to the absorption is produced. Typically, a spectrum is recorded with the spectral feature of interest in approximately the center of the spectrum. A least square fit is used to determine the amount of absorption is present. The basis set for the least squares fit is usually polynomial functions (to describe the background) together with a model of the absorption. See, e.g., U.S. patent application Ser. No. 09/640,566, to D. C. Hovde, entitled "Filtering to Measure Gas Concentrations from Spectral Features". The least squares fit of the measured spectrum returns a series of coefficients—one for each basis function. The coefficient for the model of the absorption is proportional to the amount of the absorption.

One of the problems associated with the measurement of small absorptions using wavelength modulation spectroscopy is that artifacts in the background of the absorption spectrum limit the sensitivity of the instrument because these background components interfere with the fitting procedure. These background components may be caused by the laser, by etalons, or by other absorbers present in the system. If basis functions can be designed that compensate for these artifacts, the fit can usually be improved. Unfortunately, this is extremely difficult. Careful modeling of these artifacts is not typically possible because the artifacts are too complex, often interact and vary over time. Measurement of the artifacts is also impossible because they can add in such a complex fashion that the result often looks like noise. Even worse, an average background cannot be used because of slowly varying components such as the phase of an etalon.

The method of the invention examines the background function for a moderate period of time and constructs a basis set that describes the background and the fluctuations. Periodically updating the basis functions allows for the compensation of slow drift in the system such as temperature fluctuations, mechanical instabilities, laser instabilities, etc. The effectiveness of the method of the invention is demonstrated herein with respect to a laser absorption device. After the method is demonstrated, other uses are discussed.

Start with a laser absorption device. The current of a temperature stabilized diode laser is rapidly modulated at a frequency f in order to tune the emitted light. The emitted light is sent through a sample cell containing an absorbing medium. As the laser is tuned over an absorption feature (by slowly ramping the current), the absorption causes a frequency at the second harmonic of f to be produced. A plot of the demodulated second harmonic intensity vs. current (wavelength) produces a "2f spectrum" of the absorption. A least squares fit is used to determine how much of the reference is contained in the spectrum.

Paramount to the performance of a least squares fit is proper representation of the background—etalons and artifacts present in the spectrum. Conventionally a third-to-fourth order polynomial is used to fit the background. Unfortunately, such functions are inadequate as indicated by long-term roll and drift of the measured absorbance.

The method of the invention preferably operates as follows: A least squares fit can be used to either describe a system of interest or to determine the weight of a function that may describe part of a system of interest. The weight, or coefficient, of the function of interest may correspond to the concentration of a substance such as a gas. The absorption follows a specific functional form that is included as a basis function in least squares analysis. When the fit is completed, the coefficient for the absorption basis function directly relates to the amount of absorption and hence the concentration of the absorber. However, in real world systems, there are artifacts present that that can cause errors in the measurement. These artifacts, which are referred to here as background, disrupt the fit in such a way as to cause inaccuracies in the coefficient for the absorption basis function. However, if this background can be fit appropriately, the accuracy of the fit can be restored; that is, the accuracy of the coefficient of the function of interest can be restored. Thus, it is of paramount importance to accurately model the background for purposes of the least squares fit.

The method of the invention uses a systematic approach to construct a set of functions to use in a least squares fit for modeling the artifacts, or background, in the system. This method constructs a series of orthogonal functions that describe the background. These functions, together with the function corresponding to the quantity of interest, form the basis for the least squares fit. While the basis functions describing the background are orthogonal, the basis function used for the quantity to measure may or may not be orthogonal to the background functions. In general, the basis function for the quantity to measure should not be orthogonal to the background functions. However, orthogonality of the background basis functions is not enough. The functions must be orthogonal and descriptive of the background. Therefore, the present invention uses singular value decomposition in order to determine descriptive, orthogonal functions for the basis of the least squares fit.

Figure 1:
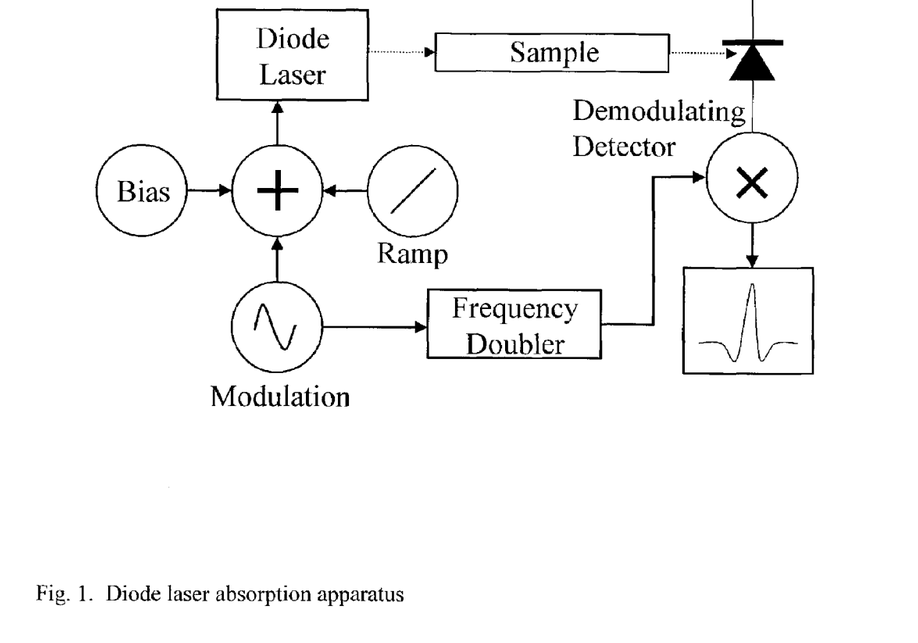

The method is demonstrated using a diode laser absorption device to measure low concentrations of water vapor in a gas. A diode laser is tuned over a selected wavelength range. A set of many spectra is taken at periodic time intervals. Sampling should be long enough to encompass several periods of oscillations in the background and/or temperature jumps of the laser. As an example, sets of 109 spectra that are 158 points long are taken over a two-day period. This forms a matrix that has 158 rows and 109 columns of sample 2f spectra denominated $\Phi_{2f}$. Another matrix contains the direct current ("DC") power of the diode laser over the wavelength scan, called $\Phi_{DC}$. Assume that the laser is not tuned onto a water line or there is no absorption from water vapor in the spectrum. The normalized spectrum is the 2f spectra divided by the DC spectrum (point-by-point) (FIG. 1). An SVD of the normalized spectrum yields:

$$\frac{\Phi_{2f}}{\Phi_{DC}} = USV^T$$

The SVD operation constructs three matrices such that $USV^T = \Phi_{2f}/\Phi_{DC}$. The matrix U contains the basis functions used to describe the background in the normalized spectra. Matrix S is a diagonal matrix that contains the weights or the amount of each vector in U that is used to describe the original matrix. Matrix V determines how each basis vector is applied to each spectrum in the original matrix. For this application, the V matrix is not used. Note that if the transpose of $\Phi_{2f}/\Phi_{DC}$ is used in the SVD, then the columns of V would provide the basis functions and the matrix U determines how each basis vector is applied to each spectrum in the original matrix.

The elegance of the SVD lies in the fact that the column vectors of U form an orthonormal basis set that describe the column vectors in the original matrix in the most compact way. Therefore, the outer product between the first column of U, the first column of V and the greatest weight, $S_{1,1}$, forms the best rank one representation of the matrix in the least squares sense. A better representation of the original matrix is the sum of the outer product of the first columns of U and V with the outer product of the second columns of U and V (multiplied by the appropriate weights). Depending on which matrix is used to provide the basis functions, the other matrix can be used to determine how the makeup of the background changes with time, which can be useful for tracking how etalons change, for example. Discussion of SVDs may be found in: G. Stewart, "Perturbation Theory for the Singular Value Decomposition", University of Maryland Computer Science Technical Report CS-TR-2539 (1990); A. Jain, *Fundamentals of Digital Image Processing*, Prentice Hall Information and Systems Sciences Series, Prentice Hall, Englewood Cliffs (1989); and W. Press, et al., *Numerical Recipies in C: The Art of Scientific Computing*, 2d ed., Cambridge University Press, Cambridge (1995). A related technique known as Empirical Orthogonal Functions ("EOF") is discussed in M. Richman, "Rotation of Principal Components", *Journal of Climatology* 6:393–335 (1986). D. Broomhead, et al., "Extracting qualitative dynamics from experimental data," *Physica* 20D, pp. 217–236 (1986), demonstrates the use of SVD for determining the dynamics in a system that varies as a function of time or other variable. This is sometimes called singular spectrum analysis (SSA).

Figure 2:
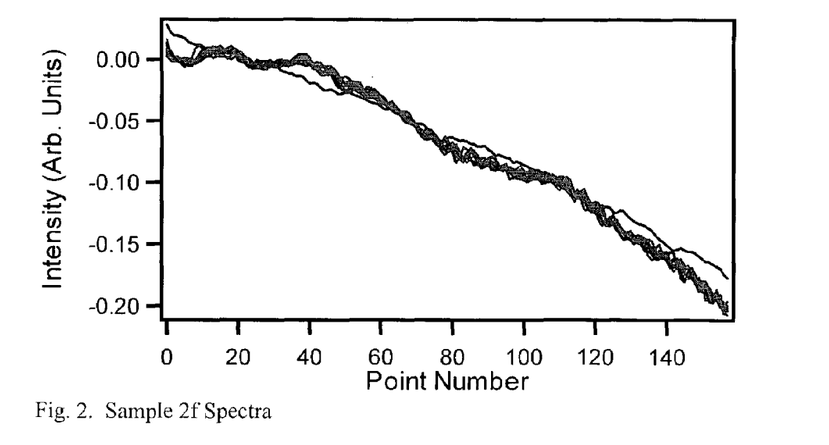
FIG. 2 is a plot of several background spectra obtained from a wavelength modulation spectroscopy system of FIG. 1. The plot is signal (y axis) versus point number (x axis). The background is not smooth and contains many features that can interfere with the measurement of the absorber species.

FIG. 2 shows the first basis function. Notice that the form is quite similar to the background of the normalized spectra. This background function is the best Rank-1 approximation of the matrix of the background vectors. To determine how many basis functions are required to be used in the fit, one can look at a plot of the weights, FIG. 3.

Figure 3:
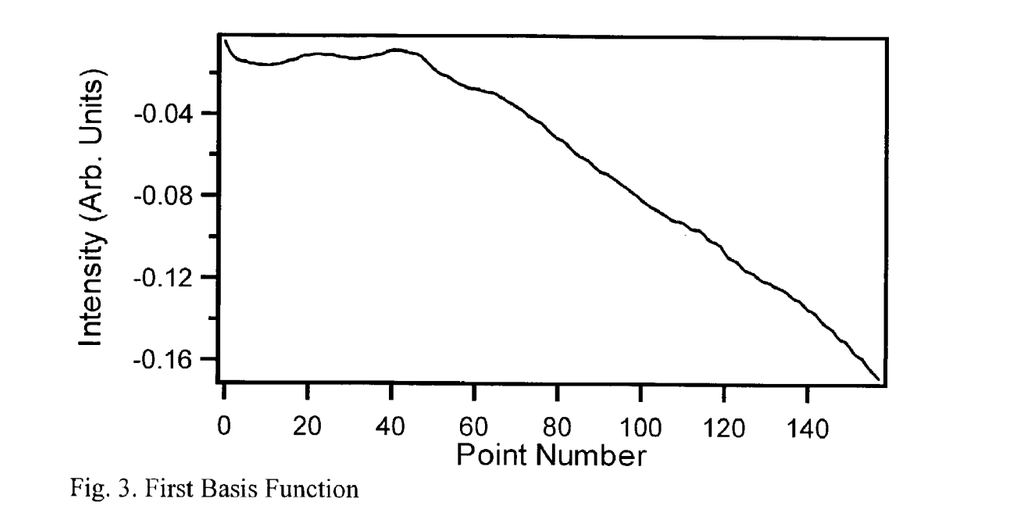
FIG. 3 is a plot of the first basis function of the background obtained by using singular value decomposition ("SVD") according to the invention. This basis function describes the major features of the background.
Figure 4:
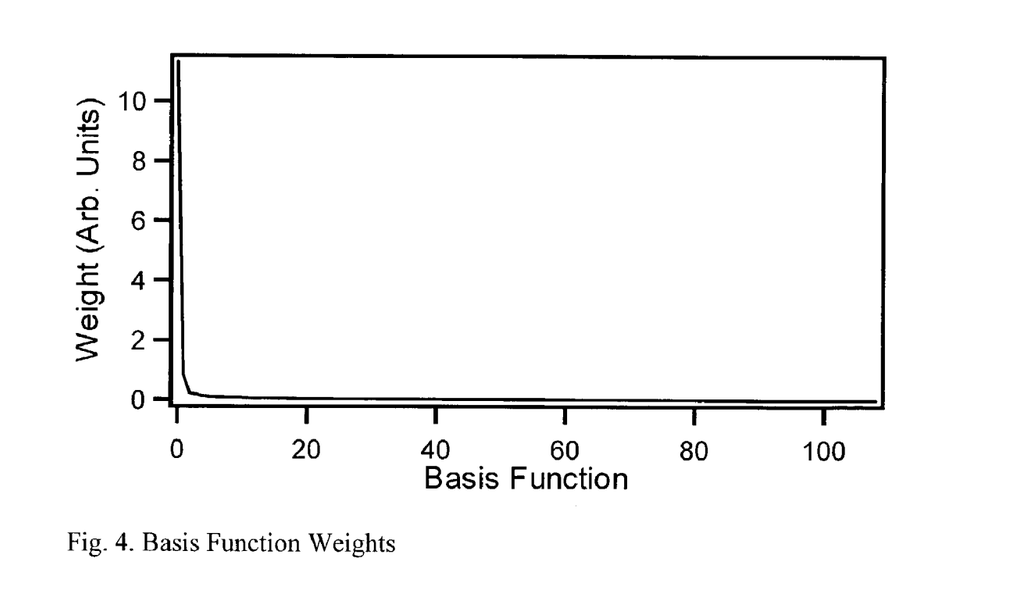
FIG. 4 is a plot of the weights obtained from the singular value decomposition. From this plot, the number of basis functions required to describe the background can be determined. This plot shows that fewer than 10 basis functions are required in the fit. Any more than 10 would only be fitting noise.
Figure 5:
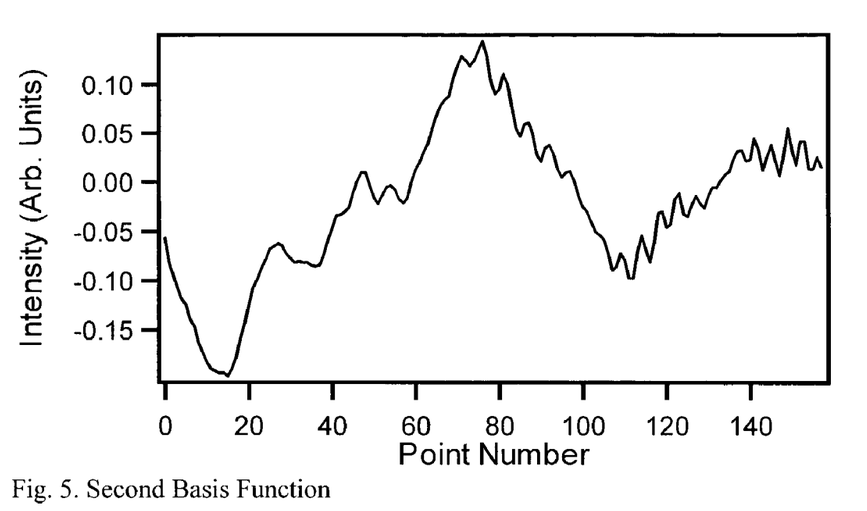
FIG. 5 is a plot of the second basis function. This basis function approximates a low frequency etalon and can interfere with the signal of interest measured by the instrument.
Figure 6:
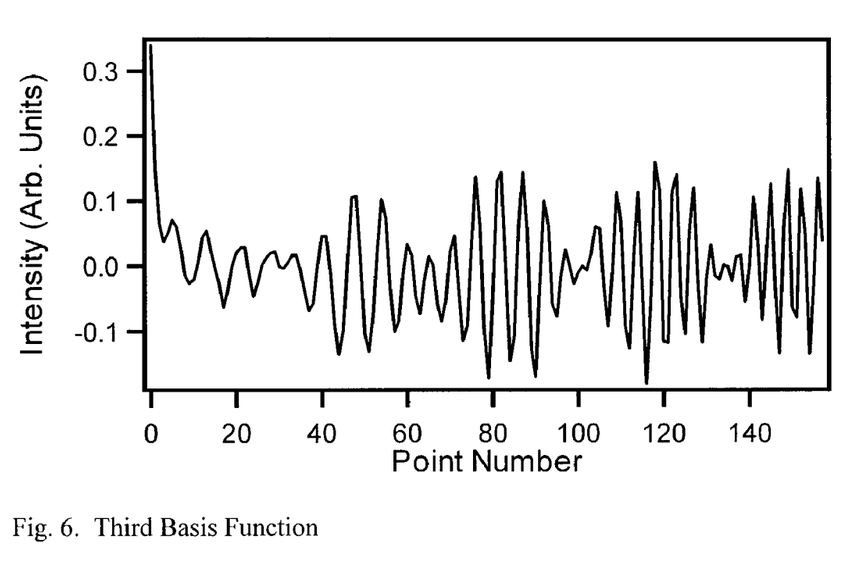
Figure 7:
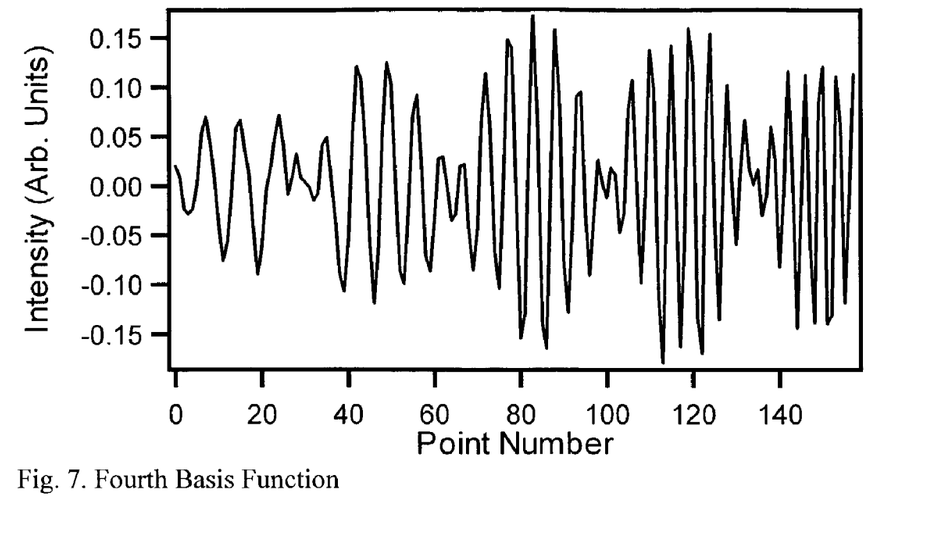
Figure 8:
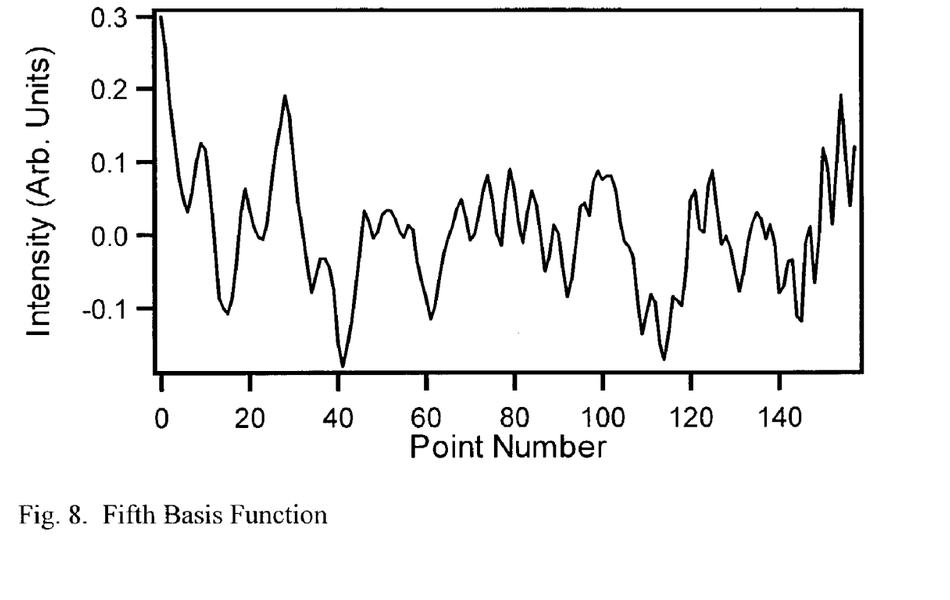
FIG. 8 is a plot of the fifth basis function. This function is beginning to have more noise-like character.
Figure 9:
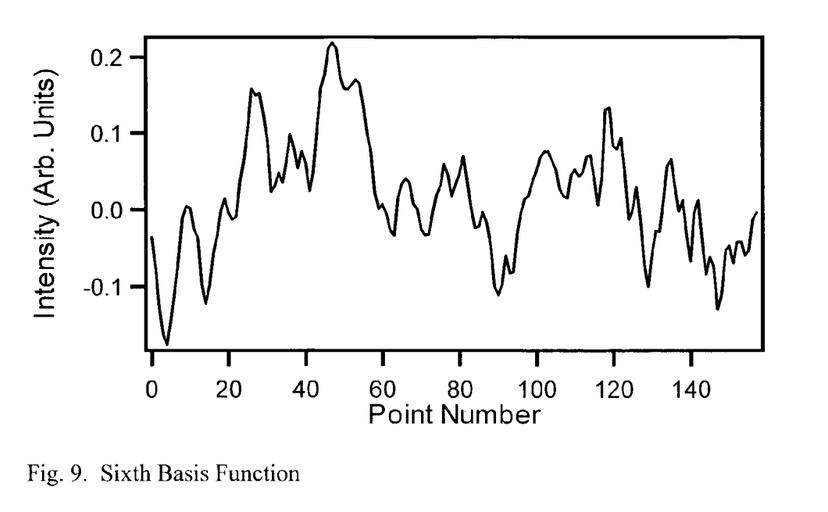
FIG. 9 is a plot of the sixth basis function. Like the fifth basis function, this function has noise-like character and shows no indication that it is a phase shifted version of the fifth basis function. Thus, no more than six basis functions are required to describe the background for this instrument. The seventh basis function is a basis function that depicts the signal of interest.

The x-axis of FIG. 3 is the rank of the weight and the y-axis is the weight value. Notice the weights are all ordered. The weights and vectors are all properly ordered by the SVD routine. For this example, six of the returned basis functions are used. (After about 10, where the weight curve flattens out, only random fluctuations are being fit.)

Performing an SVD on a set of spectra has an additional advantage of determining the number of independent functions that are responsible for the background. For example, if there are some absorbers that cause a fluctuating background, an analysis such as this can determine the number of independent absorbers (or other perturbations) that are causing the background fluctuations. This method is not limited to the cause of the perturbations. It is sensitive only to the effect of the perturbation. Inspection is used to determine the number of background functions used in the fit. The functional form of the weight function gives some guidelines. Typically, the weight function follows a function form similar to 1/(the index of the singular value). As the singular values start to follow a line asymptotically approached the x axis, the corresponding basis functions do not need to be included in the fit and usually only fit noise. Other guidelines are provided by the basis functions themselves. If the basis functions appear to be entirely random, without structure, then they may be discarded, but this is not definitive. To discard a basis function from the fit, both of the above criteria may be required.

FIGS. 5–9 show basis functions 2–6. Notice that the functions in FIGS. 5–7 have a strong sinusoidal component reminiscent of an etalon somewhere in the optical system. By examining fringe period, the spacing between the reflective surfaces can be determined. This can help to pinpoint the cause of the etalon. Thus, the analysis method of the invention can be used to diagnose problems in the system. Basis functions 3 and 4 are the same etalon, approximately 90 degrees out of phase. By examining the relative amplitude of the two basis functions, the drift rate can be determined. Basis functions 5 and 6 are beginning to look like random noise, so no more basis functions are required in the fit to describe the background.

Figure 10:
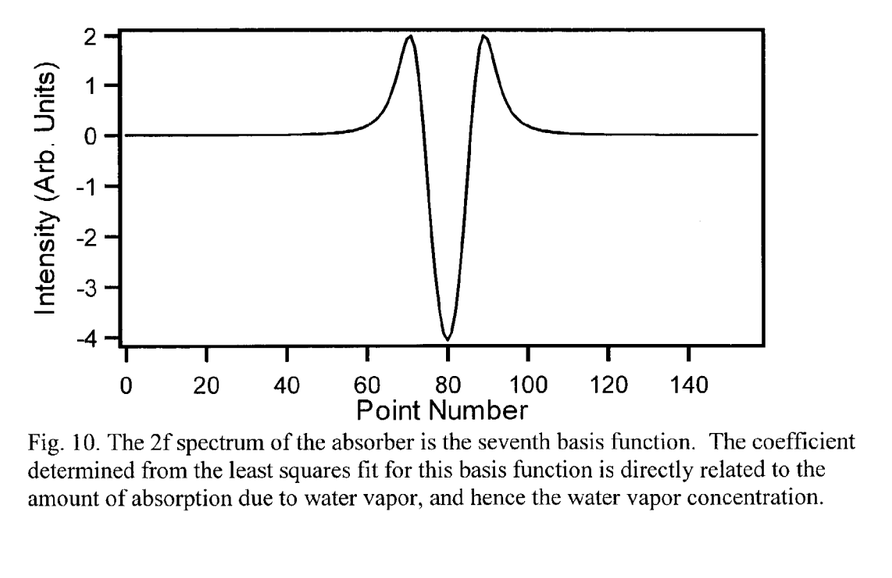
FIG. 10 is a plot of the signal of interest (not one of the background basis functions). This is the seventh basis function in the least squares fit. This function may or may not be orthogonal to the background functions.

FIG. 10 is the reference spectrum, model2f. There are now a total of 7 functions that will be used in the fit. Six functions have been obtained from the SVD while the seventh is the reference spectrum.

Figure 11:
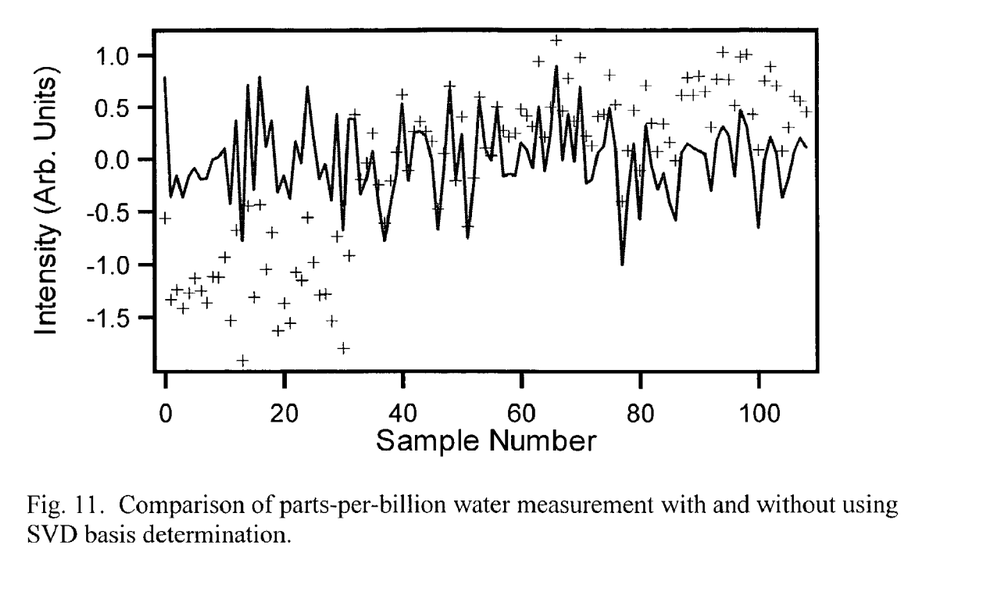
FIG. 11 compares the parts-per-billion (ppb) water level measured over time using only the model function together with a polynomial to describe the background (discrete points). The ppb water level determined using the improved basis set according to the invention is shown with the solid line. While the point-to-point scatter of the measurements is not improved, the long-term drift associated with the measurements is completely removed, greatly improving the precision of the measurement.

Plotted in FIG. 11 is the ppb level of water determined by standard least squares ("LSQ") fit using a polynomial model for the background (points) compared to a fit using the improved basis functions generated by the invention (line). One can see that most of the long term roll in the ppb level has been removed while short-term fluctuations remain unchanged.

The present invention also provides for updating basis functions in real-time. As temperature changes and aging effects, as well as other effects, cause changes in the optical properties of the system, the best basis functions can change with time. Fortunately, the basis functions can be updated "on the fly." One way that this can be accomplished is to remove all of the absorber from the system to allow only a background to be measured. Many spectra can be recorded. The new basis functions can be determined from the recorded spectra using an SVD. Alternatively, the newly recorded spectra can be combined with the previous matrix of background spectra. (To keep the matrix the same size, some earlier spectra can be removed.)

Sometimes it is not possible to completely remove the absorber from the system. In this case, the spectroscopic source can be tuned off the absorption resonance.

Tuning the spectroscopic source off resonance is not without problems, however. Many of the background artifacts are wavelength dependent; thus, tuning the laser changes the background. Therefore, another way to determine the background functions for the least square fit is to assume that the device is functioning properly and subtract out the contribution of the absorber being measured from the measured spectrum. The remainder is the background. A series of these backgrounds can be collected and used as spectra for the background calculation using an SVD.

The present invention can be employed for any application that uses a fit to quantify a parameter of interest. Examples include measuring an absorbance in the presence of large backgrounds, such as measuring oxygenation of biological molecules such as hemoglobin, and determining the amount of an audio signal in the presence of noise and background. Other applications include measuring small changes in a wavefront in the presence of a large background and feature extraction in images. Other biological applications include determining the presence of a small scattering center, such as a tumor, in the presence of a large background that could be caused by the surrounding tissue.

The method of the invention can easily be incorporated into computer software. For example, MATLAB provides SVD calculation functionality, but any of several mathematics packages or development of code independently of a package may be employed. The method can be run on software on a personal computer, mainframe, supercomputer, field programmable gate array ("FPGA"), firmware, or like hardware devices.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for segregating out background signals from a signal of interest, the method comprising the steps of:
    sampling a signal that includes the background signals over one or more periods of time;
    forming a matrix from results of the sampling step;
    calculating a matrix of basis functions via a singular value decomposition of the matrix from the forming step;
    determining a set of basis functions to employ to segregate out background signals; and
    altering an input over the one or more periods of time, thereby affecting the combined signal, wherein the altering step comprises changing current supplied to a laser of a wavelength modulation spectroscopy device.

2. The method of claim 1 additionally comprising the step of including the signal of interest in the set.

3. The method of claim 1 additionally comprising the step of subsequently using the results of the determining step to remove background signals from a subsequent measurement of a signal combining the background signals and the signal of interest.

4. The method of claim 3 comprising the step of periodically reexecuting the sampling, forming, calculating, and determining steps as the background signals become altered.

5. The method of claim 1 additionally comprising the step of employing the set of basis functions to analyze one or more likely sources of one or more background signals.

6. The method of claim 1 wherein the sampling step comprises measuring light intensity at a first harmonic frequency of a frequency generated by the laser.

7. The method of claim 6 wherein the measuring light intensity step comprises measuring light intensity at a second harmonic frequency.

8. The method of claim 7 wherein the forming step comprises dividing a matrix from the results of the sampling step by a matrix of current supplied to the laser.

9. A method for segregating out background signals from a signal of interest generated from a wavelength modulation spectroscopy device, the method comprising the steps of:
    sampling a signal that includes the background signals over one or more periods of time while changing current supplied to a laser of the wavelength modulation spectroscopy device;
    forming a matrix from results of the sampling step;
    calculating a matrix of basis functions via a singular value decomposition of the matrix from the forming step; and
    determining a set of basis functions to employ to segregate out background signals; and
    wherein the sampling step comprises measuring light intensity at a first and second harmonic frequency of a frequency generated by the laser.

10. The method of claim 9 additionally comprising the step of including the signal of interest in the set.

11. The method of claim 9 additionally comprising the step of subsequently using the results of the determining step to remove background signals from a subsequent measurement of a signal combining the background signals and the signal of interest.

12. The method of claim 11 comprising the step of periodically reexecuting the sampling, forming, calculating, and determining steps as the background signals become altered.

13. The method of claim 9 additionally comprising the step of employing one or more of the basis functions to analyze one or more likely sources of one or more background signals.

14. An apparatus for segregating out background signals from a signal of interest, the apparatus comprising:
    means for sampling a signal that includes the background signals over one or more periods of time;
    means for forming a matrix from data provided by the sampling means;
    means for calculating a matrix of basis functions via a singular value decomposition of the matrix formed by the forming means;
    means for establishing a set of basis functions to employ to segregate out background signals; and
    means for altering an input over the one or more periods of time, thereby affecting the combined signal, wherein said altering means comprises means for changing current supplied to a laser of a wavelength modulation spectroscopy device.

15. The apparatus of claim 14 additionally comprising means for including the signal of interest in the set.

16. The apparatus of claim 14 additionally comprising means for subsequently using the set to remove background signals from a subsequent measurement of a signal combining the background signals and the signal of interest.

17. An apparatus for segregating out background signals from a signal of interest generated from a wavelength modulation spectroscopy device, the apparatus comprising:
    means for sampling a signal that includes the background signals over one or more periods of time while changing current supplied to a laser of the wavelength modulation spectroscopy device;
    means for forming a matrix from data provided by the sampling means;
    means for calculating a matrix of basis functions via a singular value decomposition of the matrix formed by the forming means; and means for establishing a set of basis functions to employ to segregate out background signals; and wherein said sampling means comprises means for measuring light intensity at a first and second harmonic frequency of a frequency generated by the laser.

18. The apparatus of claim 17 additionally comprising means for including the signal of interest in the set.

19. The apparatus of claim 17 additionally comprising means for subsequently using the set to remove background signals from a subsequent measurement of a signal combining the background signals and the signal of interest.

20. Computer software for segregating out background signals from a signal of interest, the software embodied on a computer readable medium and comprising:

means for sampling a signal that includes the background signals over one or more periods of time;

means for forming a matrix from data provided by the sampling means;

means for calculating a matrix of basis functions via a singular value decomposition of the matrix formed by the forming means;

means for establishing a set of basis functions to employ to segregate out background signals; and means for altering an input over the one or more periods of time, thereby affecting the combined signal, wherein said altering means comprises means for changing current supplied to a laser of a wavelength modulation spectroscopy device.

21. The software of claim 20 additionally comprising means for including the signal of interest in the set.

22. The software of claim 20 additionally comprising means for subsequently using the set to remove background signals from a subsequent measurement of a signal combining the background signals and the signal of interest.

23. Computer software for segregating out background signals from a signal of interest generated from a wavelength modulation spectroscopy device, the software embodied on a computer readable medium and comprising:

means for sampling a signal that includes the background signals over one or more periods of time while changing current supplied to a laser of the wavelength modulation spectroscopy device;

means for forming a matrix from data provided by the sampling means;

means for calculating a matrix of basis functions via a singular value decomposition of the matrix formed by the forming means; and means for establishing a set of basis functions to employ to segregate out background signals; and wherein said sampling means comprises means for measuring light intensity at a first and second harmonic frequency of a frequency generated by the laser.

24. The software of claim 23 additionally comprising means for including the signal of interest in the set.

25. The software of claim 23 additionally comprising means for subsequently using the set to remove background signals from a subsequent measurement of a signal combining the background signals and the signal of interest.

* * * * *